United States Patent [19]

Domeshek et al.

[11] Patent Number: 4,983,730

[45] Date of Patent: Jan. 8, 1991

[54] WATER SOLUBLE CELLULOSE ACETATE COMPOSITION HAVING IMPROVED PROCESSABILITY AND TENSILE PROPERTIES

[75] Inventors: Kenneth A. Domeshek, Matthews; Karen L. Zazzara, Gastonia, both of N.C.

[73] Assignee: Hoechst Celanese Corporation, Somerville, N.J.

[21] Appl. No.: 240,875

[22] Filed: Sep. 2, 1988

[51] Int. Cl.$^5$ .......................... C08B 3/06; A61K 9/30; A61K 9/36
[52] U.S. Cl. ...................... 536/69; 424/475; 424/480; 427/3; 106/196
[58] Field of Search .................. 536/69; 424/475, 480; 427/3; 106/196

[56] References Cited

U.S. PATENT DOCUMENTS 3,482,011  12/1969  Bohrer ................................. 264/207
4,572,833  2/1986  Pedersen et al. ..................... 424/470

OTHER PUBLICATIONS

"Cellulose Acetate-Properties and Uses", Bulletin of Hercules Powder Company, 1953, pp. 13–16.

*Primary Examiner*—Nathan M. Nutter
*Attorney, Agent, or Firm*—Robert H. Hammer, III

[57]  ABSTRACT

Water soluble cellulose acetate composition having improved processability and tensile properties suitable for application as films, coatings and fibers and comprising one or more lower molecular weight water soluble cellulose acetate components and one or more higher molecular weight water soluble cellulose acetate components, and wherein the lower molecular weight water soluble cellulose acetate components have solution viscosities at least 20 percent of that of the higher molecular weight water soluble cellulose acetate components. An exemplary composition comprises from about 85 to 98 percent by weight of a lower molecular weight water soluble cellulose acetate component having a solution viscosity of form about 5 to 50 cps and from about 15 to 2 percent by weight of a higher molecular weight water soluble cellulose acetate component having a solution viscosity of greater than 100 cps.

18 Claims, No Drawings

WATER SOLUBLE CELLULOSE ACETATE COMPOSITION HAVING IMPROVED PROCESSABILITY AND TENSILE PROPERTIES

FIELD AND BACKGROUND OF THE INVENTION

The present invention relates to a water soluble cellulose acetate composition for application as films, coatings and fibers. More particularly the present invention relates to a composition comprising a lower molecular weight water soluble cellulose acetate component and a higher molecular weight water soluble cellulose acetate component.

Water soluble cellulose acetate films and fibers and processes for producing them are known in the art. U.S. Pat. No. 2,129,052 to Fordyce, U.S. Pat. No. 2,448,082 to Creamer, U.S. Pat. No. 3,482,011 to Bohrer and U.K. Pat. No. 696,903 to Davoud all disclose that water soluble and water susceptible cellulose acetate film and fibers can be produced by utilizing various esterification and/or hydrolysis techniques on cellulose acetate which is normally insoluble in water. Additionally, Russian Pat. No. 1740744 discloses using water soluble cellulose acetate as a tablet binder for use by the pharmaceutical industry.

These water soluble cellulose acetate films and fibers, however, often have limited utility because they are difficult to process or have low tensile properties or both.

SUMMARY OF THE INVENTION

To this end, the present invention provides a water soluble cellulose acetate composition which has both improved processability and tensile properties. The water soluble cellulose acetate composition comprises one or more lower molecular weight water soluble cellulose acetate components and one or more higher molecular weight water soluble cellulose acetate components. The lower molecular weight water soluble cellulose acetate components typically have viscosities at least 20 percent and preferably at least 60 percent lower than that of the higher molecular weight water soluble cellulose acetate components. For example, the composition may comprise a lower molecular weight water soluble cellulose acetate component having a viscosity of from about 5 to 50 cps and a higher molecular weight water soluble cellulose acetate component having a viscosity of greater than 100 cps. These water soluble cellulose acetate compositions have applications as films and fibers and especially as coatings for tablets for use by the pharmaceutical industry.

DETAILED DESCRIPTION OF THE INVENTION

Cellulose acetate is obtained by esterifying cotton linters or wood pulp. The term water soluble cellulose acetate is understood by persons skilled in the art to refer to cellulose acetate which dissolves in water relatively quickly and without leaving substantial amounts of insoluble residues. Typically, water soluble cellulose acetate has a degree of substitution ranging from about 0.5 to 0.9 with 0.6 to 0.8 being preferred. It is to be recognized that "degree of substitution" is just one of several conventional ways that is used to describe the type of cellulose acetate which is water soluble. Other common ways to describe this type include measuring the acetyl value or acetyl content, measured as weight percent acetyl or weight percent acetic acid. The particular method used to describe the cellulose acetate of the present invention is not critical, and whether a particular kind of cellulose acetate is water soluble will be readily apparent to those in the art. Also it is recognized that a cellulose acetate composition which is soluble in water will be soluble in other organic solvents such as formamide, N, N-dimethyformamide, dimethyl sulfoxide, pyridine and N-methyl-2-pyrrolidone, mixtures thereof and mixtures thereof with water.

The present invention provides an improved water soluble cellulose acetate composition wherein water soluble cellulose acetate components of different molecular weights are combined to form water soluble cellulose acetate blends which have improved processability and tensile properties as compared to unblended compositions of water soluble cellulose acetate. Typically, molecular weight is described in terms of solution viscosity, and water soluble cellulose acetate is marketed based on "grades" thereof depending on the solution viscosity. Using a capillary viscometer to measure the solution viscosity of a six percent solids solution, a low viscosity grade water soluble cellulose acetate has a solution viscosity of from about 5 to 50 cps, a medium/low viscosity grade water soluble cellulose acetate has a solution viscosity of from about 50 to 100 cps, a medium viscosity grade water soluble cellulose acetate has a solution viscosity of from about 100 to 250 cps and a high viscosity grade water soluble cellulose acetate has a solution viscosity of greater than about 250 cps.

As described in U.S. Pat. No. 2,129,052 to Fordyce and herein incorporated by reference, water soluble cellulose acetate is typically produced from cellulose acetate by dissolving it in acetic acid and water and thereafter continuing the deacetylation. The reaction temperature, sulfuric acid catalyst level and reaction time determine the molecular weight and resultant solution viscosity of the water soluble cellulose acetate. The water soluble cellulose acetate is typically in the form of a solid such as a powder or flake or in solution.

Water soluble cellulose acetate grades having a lower solution viscosity (low viscosity grade and medium/low viscosity grade) tend to flow easily in the liquid state and have the ability to dissolve higher amounts of solids, but in the solid state they tend to have poorer tensile properties as compared to other water soluble cellulose acetate grades having a higher viscosity. Medium viscosity grade water soluble cellulose acetate and high viscosity grade water soluble cellulose acetate are typically the opposite. They have more resistance to flow in the liquid state but have improved tensile properties in the solid state. By utilizing the present composition, a blend or mixture of grades of water soluble cellulose acetate may be formed and the processing benefits of the lower viscosity grade water soluble cellulose acetate and the tensile property benefits of the higher viscosity grade water soluble cellulose acetate are both realized. This is unexpected in that an unblended water soluble cellulose acetate composition having the same solution viscosity as the water soluble cellulose acetate composition formed from a blend of grades of water soluble cellulose acetate will have processability properties or tensile properties or both properties which are significantly poorer compared to the present blended composition. Moreover, when polymer compositions are formed from blends of similar polymer compounds having different molecular weights, an unusable product is sometimes obtained in that the poorer properties or features of these compounds are retained or accentuated.

The present composition comprises one or more lower molecular weight water soluble cellulose acetate components and one or more higher molecular weight water soluble cellulose acetate components. The compositions are formed by blending and homogenizing them together employing the components in their powder, flake, solution or melt form using agitation, melt blending, solution blending and other conventional blending and homogenizing techniques.

Preferably the solution viscosities of the lower molecular weight water soluble cellulose acetate components are at least 20 percent lower than that of the higher molecular weight water soluble cellulose acetate component and preferably are at least 60 percent lower than that of the higher molecular weight water soluble cellulose acetate components. For example, a composition comprising from about 85 to 98 percent by weight of a lower molecular weight water soluble cellulose acetate component having a solution viscosity of from about 5 to 50 cps and from about 2 to 15 percent by weight of a higher molecular weight water soluble cellulose acetate component having a viscosity of greater than 100 cps will retain the processability characteristics of the low viscosity grade water soluble cellulose acetate component and will retain the tensile properties of the higher viscosity grade water soluble cellulose acetate component. It is to be recognized that the addition of relatively low amounts of the higher molecular weight component, such as from about 1–2 percent by weight, will have an appreciable affect on the tensile properties of the composition as compared to the unblended low viscosity grade water soluble cellulose acetate composition. In general, the compositions will have improved tensile properties as compared to an unblended low viscosity grade water soluble cellulose acetate composition and improved processability properties as compared to an unblended high viscosity grade water soluble cellulose acetate composition.

Plasticizers also may be added to any of the water soluble cellulose acetate components to modify the processability and tensile properties such as by lowering the glass transition temperature and the melting point of the composition. Exemplary plasticizers include glycerin, polyethylene glycols, diethylene glycols, propylene glycol and dimethyl sulfoxide. The plasticizers typically function to facilitate processing and to increase the flexibility and toughness of the final product.

In operation, the present water soluble cellulose acetate composition is obtained by first forming a blend of one or more of the lower molecular weight components and of one or more of the higher molecular weight components preferably in their solid forms. This blend is then formed into a homogeneous solution by dissolving the blend in water using agitation or stirring. The solution is then formed into an article of manufacture such as a coating, film or fiber.

If used as a coating, a preferred application is as tablet coatings for the pharmaceutical industry. The present water soluble cellulose acetate blend is dissolved in a solution and is sprayed or atomized through a small nozzle onto a tablet. The present water soluble cellulose acetate composition may dissolve higher amounts of solids while retaining its processability. This quality permits flow through the nozzle at higher throughput, increases production capacity and results in uniformly coated tablets. Once coated, the coating must be durable and thus the improved tensile properties of the present composition are also important. Similarly, the improved processability and tensile properties facilitate the production of films using casting, melt extrusion and other film-making techniques and facilitate the production of fibers using extrusion or other fiber-making techniques.

The invention is additionally illustrated in connection with the following examples, which are to be considered as illustrative of the present invention. It should be understood, however, that the invention is not limited to the specific details of the examples.

EXAMPLE 1

90 percent by weight of a powdered, lower molecular weight water soluble cellulose acetate composition having a viscosity of 12 cps was blended using agitation with a 10 percent by weight powdered, higher molecular weight water soluble cellulose acetate composition having a viscosity of 147 cps. The powdered blend was put into solution by dissolving in water and the resistance to flow was checked visually. The solution was cast onto a sheet of glass and uniformly spread thereon. The solution was dried to form a film. The tensile strength and percent elongation of the film were measured using an Instron ® Model 1122.

EXAMPLE 2

Following the procedures of Example 1, a film comprising 60 percent by weight of a lower molecular weight water soluble cellulose acetate component having a solution viscosity of 12 cps and 40 percent by weight of a higher molecular weight water soluble cellulose acetate component having a solution viscosity of 147 cps was produced and the resistance to flow and tensile properties thereof determined.

EXAMPLE 3

Following the procedures of Example 1, a film comprising 45 percent by weight of a lower molecular weight water soluble cellulose acetate component having a solution viscosity of 12 cps and 55 percent by weight of a higher molecular weight water soluble cellulose acetate component having a solution viscosity of 147 cps was produced and the resistance to flow and tensile properties thereof determined.

EXAMPLE b 4–5

For comparison purposes, following the procedures of Example 1, films comprising 100 percent low viscosity grade water soluble cellulose acetate having a solution viscosity of 12 cps (Example 4) and a composition comprising 100 percent medium viscosity grade water soluble cellulose acetate having a solution viscosity of 147 cps (Example 5) were produced and the resistance to flow and tensile properties thereof determined.

Table 1 illustrates the resistance to flow and tensile properties of the compositions of Examples 1–5 and includes measurements for specific tensile properties, namely the tensile strength and the percent elongation.

TABLE 1

| Example No. | Resistance to Flow | Tensile Strength (psi) | % Elongation |
|---|---|---|---|
| 1 | Low | 7185 | 3.79 |

TABLE 1-continued

| Example No. | Resistance to Flow | Tensile Strength (psi) | % Elongation |
|---|---|---|---|
| 2 | Low | 7163 | 7.63 |
| 3 | Low | 7522 | 10.02 |
| 4 | Low | 3261 | 1.93 |
| 5 | High | 7299 | 7.65 |

As is readily apparent, a water soluble cellulose acetate composition produced according to Examples 1-3 results in a product which has the processability characteristics of a lower viscosity water soluble cellulose acetate, namely its resistance to flow is low, and has the higher tensile properties of a higher viscosity water soluble cellulose acetate. The unblended low viscosity grade water soluble cellulose acetate (Example 4) on the other hand has poor tensile properties and the high viscosity grade water soluble cellulose acetate (Example 5) is resistant to flow.

The principles, preferred embodiments and modes of operation of the present invention have been described in the foregoing specification. The invention which is intended to be protected herein, however, is not to be construed as limited to the particular forms disclosed since those are to be regarded as illustrative rather than restrictive. Variations and changes may be made by those skilled in the art without departing from the spirit of the invention.

That which is claimed is:

1. A water soluble cellulose acetate composition having improved processability and tensile properties suitable for application as films, coatings and fibers and comprising one or more lower molecular weight water soluble cellulose acetate components and one or more higher molecular weight water soluble cellulose acetate components, and wherein said lower molecular weight water soluble cellulose acetate components have solution viscosities at least 20 percent lower than that of said higher molecular weight water soluble cellulose acetate components.

2. A water soluble cellulose acetate composition according to claim 1 additionally including a plasticizer.

3. A water soluble cellulose acetate composition according to claim 2 wherein said plasticizer is selected from the group consisting of glycerin, polyethylene glycols, diethylene glycols, propylene glycol and dimethyl sulfoxide.

4. A water soluble cellulose acetate composition according to claim 1 wherein said higher molecular weight component is present in an amount greater than about 1 percent by weight.

5. A water soluble cellulose acetate composition according to claim 1 wherein said lower molecular water soluble cellulose acetate components have solution viscosities of at least 60 percent lower than that of said higher molecular weight water soluble cellulose components.

6. A coating comprising the water soluble cellulose acetate composition of claim 1.

7. A pharmaceutical tablet coated with the coating composition of claim 6.

8. A water soluble cellulose acetate composition having improved processability and tensile properties suitable for applications as films, coatings and fibers and comprising a low molecular weight water soluble cellulose acetate component having a solution viscosity of from about 5 to 50 cps and a higher molecular weight water soluble cellulose acetate component having a solution viscosity of greater than about 100 cps.

9. A water soluble cellulose acetate composition according to claim 8 additionally including a plasticizer.

10. A water soluble cellulose acetate composition according to claim 9 wherein said plasticizer is selected from the group consisting of glycerin, polyethylene glycols, diethylene glycols, propylene glycol and dimethyl sulfoxide.

11. A water soluble cellulose acetate composition according to claim 8 wherein said higher molecular weight component is present in an amount greater than about 1 percent by weight.

12. A coating comprising the water soluble cellulose acetate composition of claim 8.

13. A pharmaceutical tablet coated with the coating composition of claim 12.

14. A water soluble cellulose acetate powdered blend having improved processability and tensile properties comprising from about 85 to 98 percent by weight of a low molecular weight water soluble cellulose acetate component having a solution viscosity of from about 5 to 50 cps and from about 15 to 2 percent by weight of a higher molecular weight water soluble cellulose acetate component having a solution viscosity of greater than 100 cps.

15. A water soluble cellulose acetate composition according to claim 14 additionally including a plasticizer.

16. A water soluble cellulose acetate composition according to claim 15 wherein said plasticizer is selected from the group consisting of glycerin, polyethylene glycols, diethylene glycols, propylene glycol and dimethyl sulfoxide.

17. A coating comprising the water soluble cellulose acetate composition of claim 14.

18. A pharmaceutical tablet coated with the coating composition of claim 17.

* * * * *